(12) United States Patent
Rajagopalan et al.

(10) Patent No.: US 8,179,141 B2
(45) Date of Patent: May 15, 2012

(54) METHOD AND DEVICE FOR MEASURING THE CONDUCTIVITY OF A PURE OR ULTRAPURE LIQUID

(75) Inventors: Pascal Rajagopalan, Aulnay-sous-Bois (FR); Aristotelis Dimitrakopoulos, St. Martin de Nigelles (FR); Celine Le Ninivin, Vernouil sur Seine (FR); Antony Vanheghe, Asnieres sur Seine (FR)

(73) Assignee: EMD Millipore Corporation, Billerica, MA (US)

( * ) Notice: Subject to any disclaimer, the term of this patent is extended or adjusted under 35 U.S.C. 154(b) by 302 days.

(21) Appl. No.: 12/455,351

(22) Filed: Jun. 1, 2009

(65) Prior Publication Data

US 2009/0315571 A1    Dec. 24, 2009

(30) Foreign Application Priority Data

Jun. 23, 2008 (FR) ...................... 08 54130

(51) Int. Cl.
*G01N 27/02* (2006.01)
(52) U.S. Cl. ......... 324/442; 324/439; 324/693; 324/722
(58) Field of Classification Search .................. 324/444, 324/442, 447, 722
See application file for complete search history.

(56) References Cited

U.S. PATENT DOCUMENTS

| | | | | |
|---|---|---|---|---|
| 4,118,663 A | * | 10/1978 | Barben, II | 324/443 |
| 5,260,663 A | * | 11/1993 | Blades | 324/442 |
| 5,448,178 A | * | 9/1995 | Chen et al. | 205/775.5 |
| 6,232,786 B1 | * | 5/2001 | Barnett | 324/691 |
| 6,369,579 B1 | * | 4/2002 | Riegel | 324/439 |
| 6,664,793 B1 | * | 12/2003 | Sampson et al. | 324/439 |
| 7,772,854 B2 | * | 8/2010 | Rezvani | 324/691 |
| 2003/0173976 A1 | * | 9/2003 | Wiegand et al. | 324/603 |
| 2007/0024287 A1 | | 2/2007 | Graves et al. | |

FOREIGN PATENT DOCUMENTS

| | | |
|---|---|---|
| EP | 0 672 448 | 9/1995 |
| FR | 655276 A | 4/1929 |
| JP | 7-32562 U | 6/1995 |
| WO | 88/01740 A1 | 3/1988 |
| WO | 2006/036929 | 4/2006 |

OTHER PUBLICATIONS

International Conference on Information, Communications and Signal Processing ICICS '97 Singapore, Sep. 9-12, 1997; J.G. Liu et al.; "Application of Discrete Fourier Transform to Electronic Measurements"pp. 1257-1261.
French Search Report dated May 14, 2009.

(Continued)

*Primary Examiner* — Richard Isla Rodas
(74) *Attorney, Agent, or Firm* — Nields, Lemack & Frame, LLC

(57) ABSTRACT

The invention relates to a method of measuring the conductivity of a pure or ultrapure liquid, notably water, using electrodes, characterized in that it consists in determining the conductivity by modeling the liquid in the form of an equivalent electrical circuit diagram comprising a resistor R, a capacitor Cp in parallel with the resistor R, and a series capacitor Cs. It also relates to a device for implementing this method and a purification system incorporating such a device.

16 Claims, 3 Drawing Sheets

OTHER PUBLICATIONS

Japanese Communication, with English translation, mailed Aug. 30, 2011 in corresponding Japanese Patent Application No. JP 2009-137880.

European Search Report/Written Opinion mailed Jul. 15, 2009 in corresponding European Patent Application No. EP 09290429.1.

European Communication mailed Sep. 2, 2010 in corresponding European Patent Application No. EP 09290429.1.

European Communication mailed Mar. 29, 2011 in corresponding European Patent Application No. EP 09290429.1.

Mikrochimica Acta (Wien), vol. 76, No. 3-4, 1981, II, pp. 277-288, XP007914607, presented at the 8th International Microchemical Symposium, Graz, Aug. 25-30, 1980, "The Production and Characterization of Ultrapure Water for Microanalysis and Microchemistry", Petrick, et al.

Hach Ultra Analytics data sheet, polymetron, Jan. 1, 2005, pp. 1-4, XP007917764, "Conductivity, resistivity, concentration, pH, ORP Transmitter Model 9100".

* cited by examiner

METHOD AND DEVICE FOR MEASURING THE CONDUCTIVITY OF A PURE OR ULTRAPURE LIQUID

BACKGROUND OF THE INVENTION

The present invention concerns a method of measuring the conductivity of a pure or ultrapure liquid, notably water.

Measuring the conductivity of a liquid is important in many industrial fields necessitating the use of ultrapure water, in particular the chemical, pharmaceutical, medical and electronics industries.

The conductivity of an aqueous solution is measured by measuring the resistance of that solution across a conductivity measuring cell that generally consists of at least two conductive material components forming electrodes.

A conductivity measuring cell is defined by its cell constant, which proportionately links the measured resistance to the conductivity of the solution. The cell constant determines the accuracy of the cell's measurements. It is therefore necessary to use cells with a low constant to measure the conductivity of an ultrapure liquid.

The conductivity measurement is affected by the geometry of the cell: the total area of the electrodes (s) and the distance between them (L). These two parameters define the cell constant $k=L/s$.

Conductivity is a measure of the flow of electrons through a substance. It is directly proportional to the ion concentration, the charge on the ions (valency), and their mobility. Their mobility is a function of temperature and, consequently, the measured conductivity also depends on temperature.

In theoretically pure water, the only two kinds of ions present result from the dissociation of water into H+ ions and OH− ions.

At 25° C. the theoretical conductivity of a sample of water free of ionic contamination is 0.055 μS/cm, i.e. its resistivity (resistivity is the reciprocal of conductivity) is 18.2 MΩ·cm. The resistivity of a sample is determined from the equation $\rho=R/k$, proportionately relating the measured resistance R of the sample and the cell constant k. Water is considered pure or ultrapure for resistivity values greater than 1 MΩ·cm.

One valuable application of water conductivity measurement is to any purification system including a water conductivity or resistivity sensor.

When measuring conductivity, it is necessary to apply a potential difference to the terminals of the electrodes immersed in the solution. A potential difference in the form of electrical pulses induces a current related to the area of the electrodes. The greater the area of the electrodes, the lower the cell constant and the commensurately more accurate the measured current. Applying a potential difference also creates resistance and capacitance phenomena throughout the electrical circuit. In particular a capacitance that is directly linked to the geometry of the cell appears at the electrode-solution interface. A small cell with a low constant induces a high capacitance.

A conductivity measuring cell immersed in water is conventionally modeled by an equivalent electrical circuit representing the resistance and capacitance effects of the system.

The conventional approach ignores or compensates capacitance and resistance effects specific to the electrodes; thus the model of the water between the electrodes becomes purely resistive or, after simplification of the model, is assigned a series capacitance.

For example, in the prior art the capacitance effects of the cell are compensated by regular calibration and by using electrodes with an area that is sufficiently large to reduce the phenomenon. One way to solve this problem is to immerse the conductivity measuring cell regularly in a solution of known resistivity and recalculate a cell constant to take account of the state of the electrodes.

Moreover, to be able to use the simplified model, and in order to reduce the risk of polarization, it is necessary to use electrical signals at a frequency that is accurately chosen as a function of the quality of the sampled water.

There are various prior art methods for determining the resistivity of a liquid. The methods described hereinafter are based on water modeled by an equivalent electrical circuit consisting of a capacitor in series with a resistor.

The central sampling method described in international patent application WO 88/01740 consists in periodically exciting the conductivity measuring cell. The output signal of the cell is analyzed over two different time periods during which the capacitance effects inherent to the cell are different. The signal obtained during the first interval is corrected for the capacitance effects on the basis of the signal differences between the two time intervals. The central sampling method and short wires eliminate from the solution equations the capacitance effects of the wires and the electrodes.

A second method for determining the resistivity of a pure or ultrapure liquid described in US patent application 2007/0024287 measures the alternating current passing through the conductivity measuring cell. The resistivity of the liquid is then calculated from the impedance difference between signals at different frequencies. An alternating electrical current at a precisely defined frequency is applied to the terminals of the conductivity measuring cell. The current is measured and the operation is repeated with a signal at a different frequency. The measured values being proportional to the impedances of the cell, the difference between the impedances obtained at the different frequencies can be used to calculate the serial capacitance and resistance effects of the sample. It is then possible, for a given frequency, to determine mathematically the resistivity of the liquid tested, including compensation of capacitance effects.

The above methods have limitations. Firstly, they limit the size of the electrodes and the cell constant. Then, to limit polarization, a conductivity measuring cell must be used at a particular frequency, as a function of a limited range of conductivity values of the liquid concerned. Finally, aging of the cell electrodes (passivity, corrosion, etc.) causes modification of the capacitance at the electrode-solution interface which cannot be controlled.

The conductivity of a small sample can be measured using a conductivity measuring cell provided with micro-electrodes, as described in French patent application No. 0655276, for example. This is because of the small size of the electrodes and because a high level of performance of the sensor, i.e. a low cell constant, is maintained. It has nevertheless been found that using micro-electrodes, thanks to their small size, can produce large capacitance effects, which can no longer be ignored. It is then necessary to revise the model of the cell in water.

As indicated above, the theoretical model of a conductivity measuring cell immersed in water is represented by an equivalent electrical circuit diagram consisting of numerous resistors and capacitors, in series or in parallel, characterizing the behavior of the components of the system. The occurrence of capacitance phenomena when using micro-electrodes must then be taken into account in the model. It is immediately apparent that adding a capacitor in series with the single resistor of the simplified model is no longer sufficient to represent the electrical behavior of the cell during tests.

SUMMARY OF THE INVENTION

The present invention therefore uses a new model for a conductivity measuring cell immersed in water, including in the equivalent electrical circuit diagram a capacitor in series with a parallel-connected combination of a resistor and a capacitor. The benefit for micro-electrodes of this new model is considerable. It is nevertheless important to note that this new model does not apply only when using micro-electrodes, and that it is equally applicable to concentric electrodes and to measurements on solutions of lower quality.

Thanks to the present invention, it is generally possible to take into account the effects of serial and parallel capacitances in the electrical model of highly pure water to measure the conductivity accurately. The invention also detects foreign bodies present in the sample.

To be more precise, the present invention proposes a method of measuring the conductivity of a pure or ultrapure liquid, notably water, using electrodes, characterized in that it consists in determining the conductivity by modeling the liquid in the form of an equivalent electrical circuit diagram comprising a resistor R, a capacitor Cp in parallel with the resistor R, and a series capacitor Cs.

According to preferred features, where appropriate combined:
  it includes the steps of applying series of reference excitation signals at different frequencies, reconstructing the spectrum of the output signal by aggregating discrete measurements taken at the given frequencies, comparing the reconstructed empirical signal with a theoretical model, and minimizing the difference between the theoretical model and the empirical signal obtained to extract therefrom the triplet R, Cp, Cs;
  the reconstructed spectrum of the output signal is subjected to temporal interpolation to increase the resolution of the signals at intermediate frequencies and/or to extrapolation of the frequencies in order to take into account frequencies that are inaccessible experimentally;
  the comparison is effected between the Fourier transformed function of the reconstructed empirical temporal signal and the Fourier transform of the theoretical model or between the reconstructed empirical temporal signal and the inverse Fourier transform of a Fourier transform of the theoretical model;
  the minimization step uses differential norm multidimensional non-linear minimization, preferably in the form of the Powell method or the Simplex method with linear programming;
  it is further determined if the extracted triplet R, Cp, Cs corresponds to a situation of disturbance of the measurement and, if so, the nature of the disturbance;
  the determination step uses a belonging probability calculation;
  the disturbance corresponds to the presence of a foreign body, notably a particle, a non-miscible contaminant, or a gas bubble;
  the excitation signals are applied in the form of pulses, preferably squarewave pulses;
  the range of frequencies of the excitation signals is from 50 Hz to 5 kHz or from 100 kHz to 20 MHz; and
  the conductivity is measured by means of micro-electrodes.

The invention also relates to a device for measuring conductivity of a pure or ultrapure liquid, notably water, characterized in that it includes control means for executing the method defined above.

According to preferred features of this device, where appropriate combined:
  the control means include a microcontroller;
  the microcontroller is connected to a conductivity measuring cell excited by a pulse generator or a reference signal generator; and
  the or each conductivity measuring cell is provided with micro-electrodes.

The invention finally relates to a water purification system including the above conductivity measuring device.

BRIEF DESCRIPTION OF THE DRAWINGS

Other advantages of the present invention will become apparent on reading the following description, which is given with reference to the drawings, in which.

DETAILED DESCRIPTION OF THE INVENTION

It should be noted that the following description is given by way of nonlimiting example.

To measure the conductivity of a pure or ultrapure liquid, such as water, it is necessary to model it by means of an equivalent electrical circuit diagram embodying the cell-solution interface and the electrical properties of the liquid.

The electrical effects of the connecting wires between the electrodes and the surrounding electronic systems are also taken into account, and are modeled by a capacitor.

The resistances of the model, which are of the order of one ohm, can be ignored compared to the resistivity of the pure or ultrapure liquid.

Figure 1:
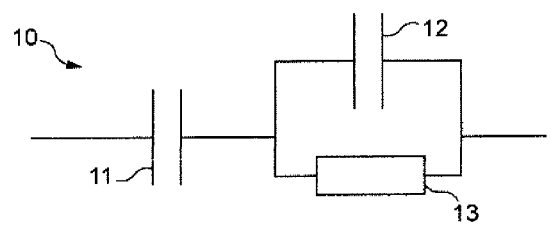
FIG. 1 represents the equivalent electrical circuit model of the present invention for a highly pure liquid.

The model can then be revised and the liquid modeled in accordance with the present invention by the equivalent circuit 10 shown in FIG. 1. This comprises a capacitor 11 in series with a parallel-connected combination of a capacitor 12 and a resistor 13.

Figure 2:
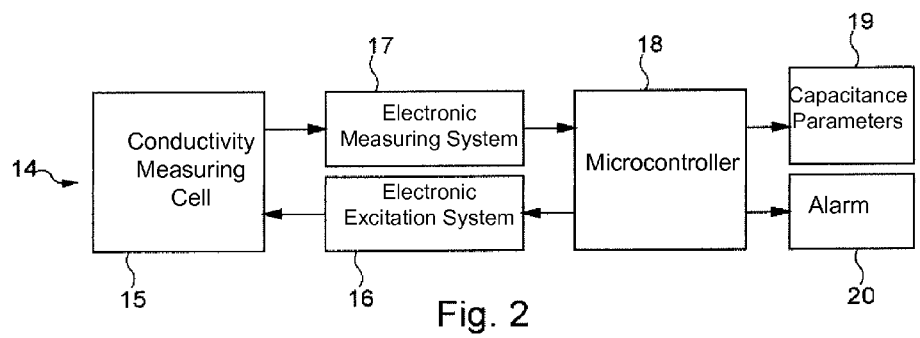
FIG. 2 is a general diagram of a method of the present invention for determining the conductivity and parameters of sampled water.

The conductivity of the tested sample is determined by a method conforming to the general diagram 14 (FIG. 2). This method is based on the characteristics of the liquid, notably in a Fourier or Laplace space, and detects abnormal situations by comparing the characteristics of the tested liquid with various predetermined models.

To be more precise, the general diagram 14 shows a conductivity and temperature measuring cell portion 15 excited by an electrical pulse from an electronic excitation system 16 controlled by an algorithm executed by a microcontroller 18.

The temperature measuring electronics are conventional (for example a Wheatstone bridge) and are not described in more detail here. Note, however, that they link the measured parameters of the liquid to temperature and therefore take into account the influence of temperature on those parameters.

The excitation applied to the conductivity measuring cell 15 induces an electrical current between its two electrodes. The response to the excitation, disturbed by its passage through the solution, is routed to the microcontroller 18 by an electronic measuring system 17.

The received signal is then processed and interpreted by the algorithm of the microcontroller 18, which outputs the resistance and capacitance parameters 19 of the tested solution. The algorithm of the microcontroller 18 triggers an alarm 20 if the sample in question is contaminated, for example by solid particles or air bubbles.

Figure 3:
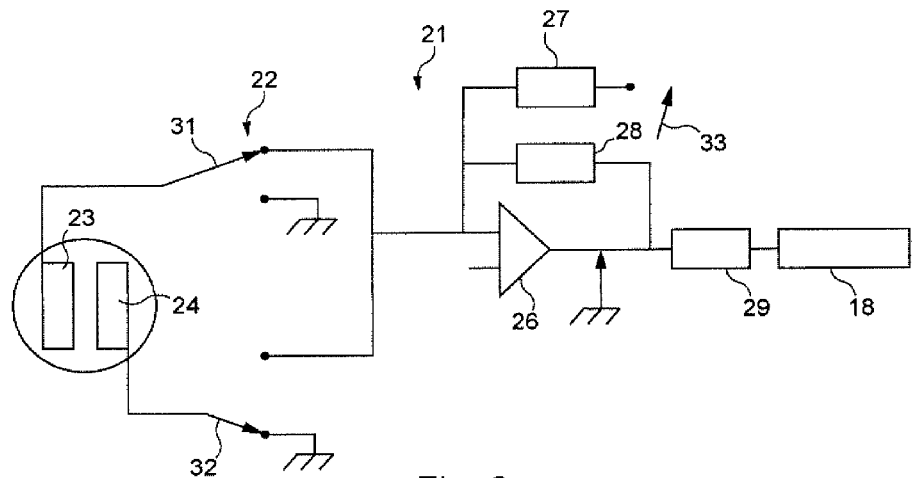
FIG. 3 is an electronic circuit diagram of one embodiment of a system of the present invention for measuring electrical properties of water.

As represented by the circuit 21 in FIG. 3, the electronic excitation and measurement part of one embodiment of the present invention includes a pulse generator 22 or a reference signal (squarewave, sinusoid, sawtooth, etc.) generator. This generator can be a voltage or current source, but here it is designed to have the following two characteristics:

the peak-to-peak voltage between the electrodes never exceeds 1.23 V, to avoid dissociation and autoprotolysis of the water, and the mean voltage of the signal is zero.

Although a pulse defined by a current source can be used, excitation by a voltage source is more practical to use and control in an electronic circuit. Any type of pulse can be used: squarewave, sinusoid, sawtooth, etc. Here this signal is of limited bandwidth and meets the above conditions, of course. In practice it is preferable to use a squarewave signal because such signals are easier to manipulate with an electronic circuit.

The pulse generator 22 feeds a conductivity measuring cell the two electrodes 23 and 24 whereof (here micro-electrodes) are shown in FIG. 3. The electrodes 23 and 24 are controlled by switches 31 and 32 of the generator 22 to excite both electrodes with the same reference signal, thereby eliminating the risk of dissymmetry.

The signal from the cell is amplified and processed by an operational amplifier 26, and resistors 27 and 28 accurately set the signal gain. A reference signal $V_{REF}$ is applied to an input of the operational amplifier 26. The resistors 27 and 28 are selected by a gain resistor selector 33. The voltage signal Vs from the operational amplifier 26 is converted from an analog signal to a digital signal by an analog-to-digital converter 29, and the signal is then routed to the microcontroller 18.

Figure 4:
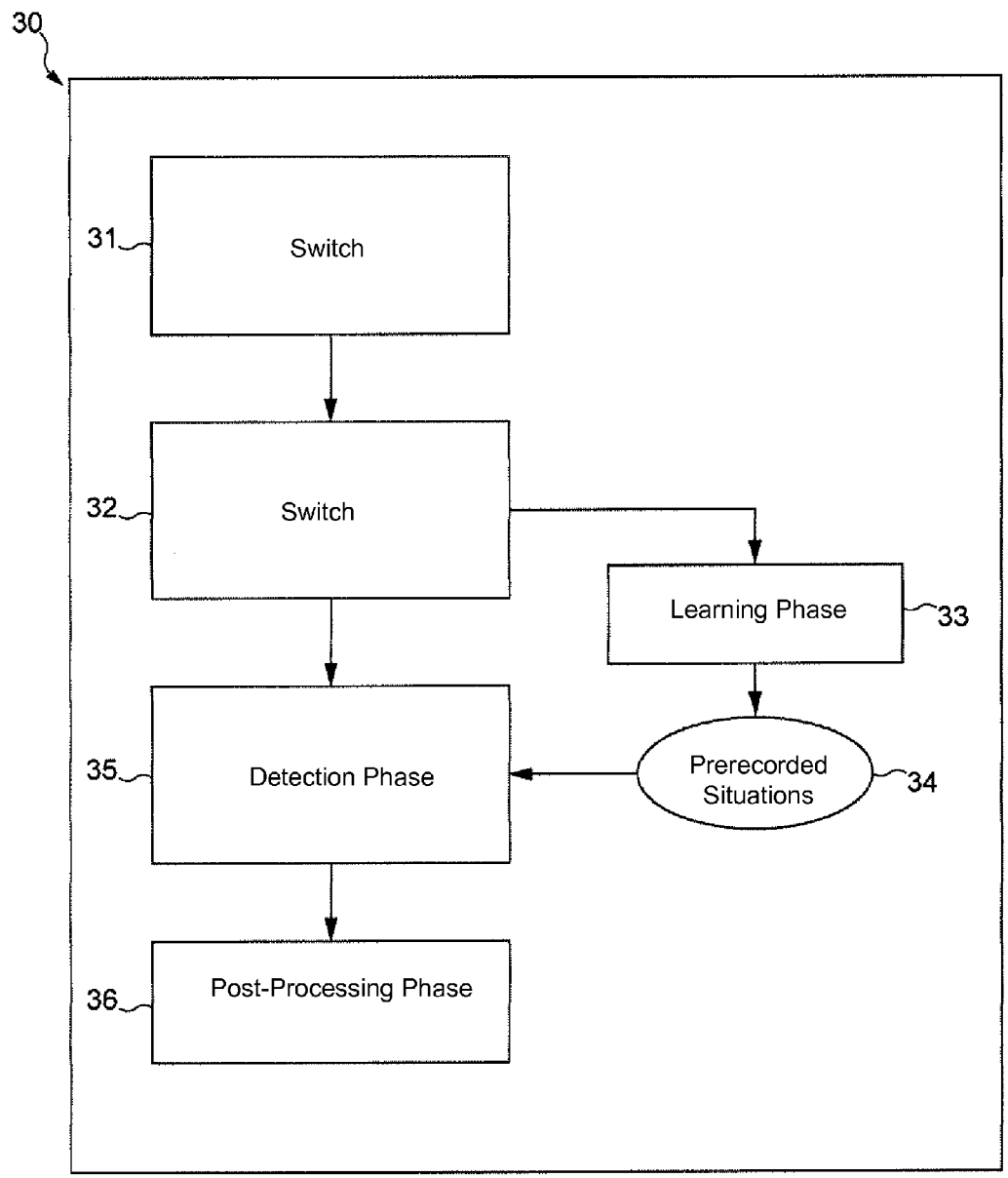
FIG. 4 represents the algorithm of one embodiment of a microcontroller of the present invention.

Here (see FIG. 4) an algorithm 30 of the microcontroller 18 for determining parameters of the system (conductivity deduced from the resistance, series capacitance and parallel capacitance) includes firstly a preprocessing phase 31 for improving the quality of the digital signal to facilitate its analysis.

The signal is then analyzed during a vectorial extraction phase 32 to determine the parameters of the system. These are routed to a database to associate them with a situation tested during a learning phase 33. The parameters from the extraction phase 32 are then compared to the prerecorded situations 34 during a detection phase 35.

Depending on whether the parameters identified come from a contaminated or uncontaminated sample, the alarm and post-processing phase 36 triggers an alert 20 in respect of the quality of the sample and/or communicates its parameters 19 (cf. FIG. 2) to a display unit that is not shown in the figures.

Figure 5:
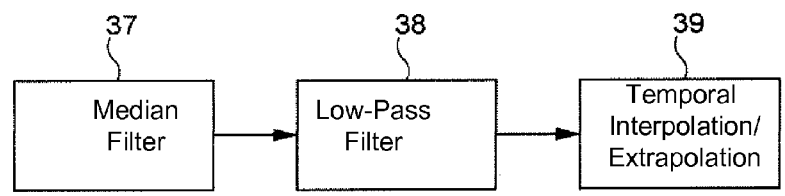
FIG. 5 shows in more detail a signal preprocessing phase of the algorithm.

In practice, a series of reference excitation signals is applied to the terminals of the electrodes. Each signal corresponds to a given frequency between 50 Hz and 5 kHz. Referring to FIG. 5, during the preprocessing phase 31, the digitized signal from the analog-to-digital converter 29, corresponding to a given frequency, is filtered, here by a median filter 37, to eliminate aberrant measurement points. It is then subjected to low-pass filtering 38 to eliminate high frequencies. By aggregating all the series of digital signals, the spectrum of the output signal is reconstructed for the given frequencies in the form of a curve of voltage as a function of period. Finally, the signal is subjected to temporal interpolation and extrapolation 39 to increase the resolution at intermediate frequencies and to sweep a range of frequencies that are not accessible experimentally. From twenty discrete measurements, for example, a spectrum of 200 values of voltage as a function of frequency can be constructed, sweeping a range from 100 Hz to 5 kHz. This method of processing the signal produces a greater quantity of data at high and low frequencies and avoids the loss of measuring time necessary to sweep the entire frequency spectrum with high resolution. The measured signal is at this stage a preprocessed temporal signal with good resolution and a good signal-to-noise ratio, ready to be analyzed.

Figure 6:
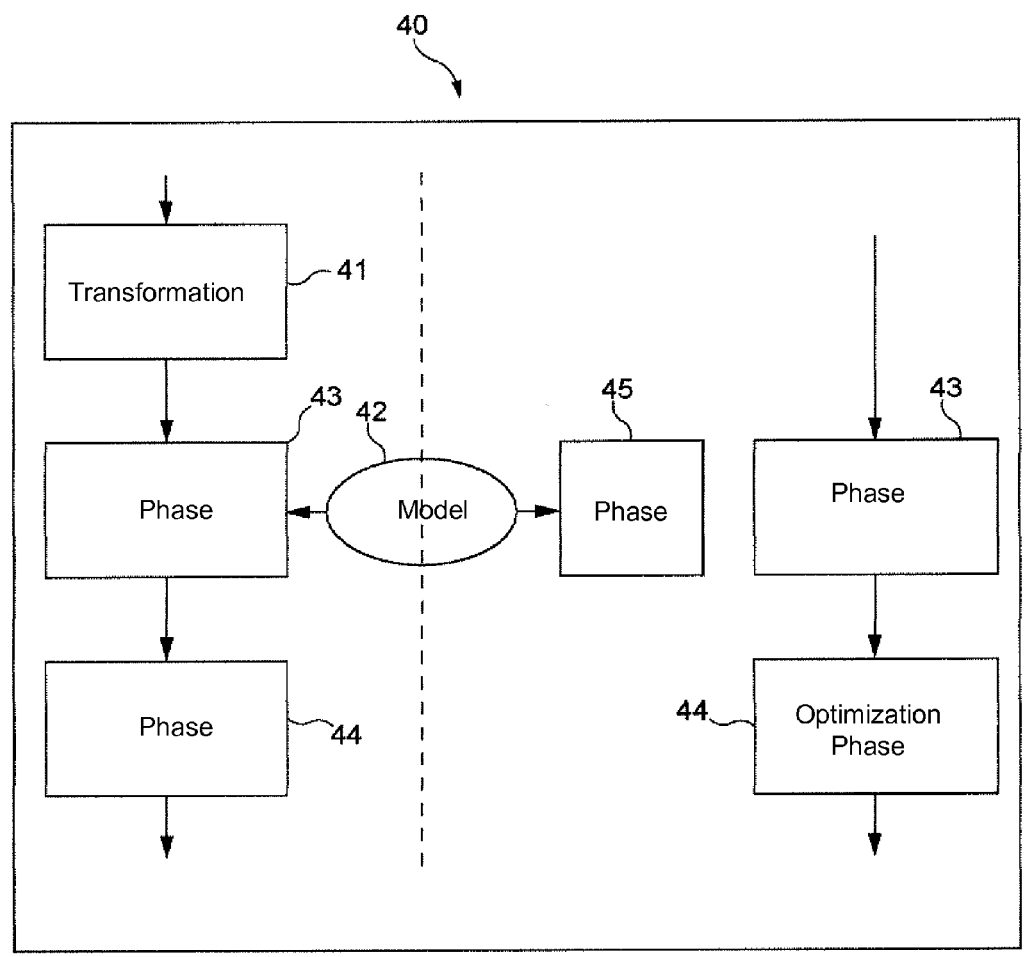
FIG. 6 shows in more detail a phase of the algorithm that determines parameters of the tested sample.

Here (see FIG. 6), the parameters of the system (the conductivity deduced from the resistance R, the series capacitance Cs and the parallel capacitance Cp) are determined using an algorithm 40 applying the extraction phase 32 to extract the solution triplet (R, Cs, Cp). The preprocessed (notably interpolated) temporal signal from the preprocessing phase 31 can be processed by two methods.

The first way of processing the preprocessed temporal signal (see the left-hand portion of FIG. 6) begins with a transformation 41 to obtain its transfer function in a Fourier or Laplace space. The fast Fourier transform function (FFT) obtained in this way is compared with the FFT of the model 42 of the liquid, which corresponds to theoretical parameters of the output signal. In the case of excitation by a squarewave signal, the model of the output signal is given by the following equation, in which T is the duration of the pulse:

$$H(j\omega) = (1 - e^{-j\omega T}) \frac{1}{j\omega C_S} + \frac{R}{1 + j\omega R C_P}$$

Comparison of the Fourier transform function obtained experimentally and that obtained from the theoretical model is effected during a phase 43 of establishing a differential norm between the empirical vector and the model vector. Differences between the experimental and theoretical results are determined during this phase. At this stage of the algorithm determining the solution vector (R, Cs, Cp), the disparities between the two transfer functions are optimized during a phase 44 of multidimensional non-linear minimization of the differential norm between the model and the signal for which an adjustment is being effected. Thanks to this optimization, the differences tend toward zero on modifying the values of the three parameters of the theoretical model. It is effected using mathematical optimization methods, for example of the kind using calculation of first derivatives (gradient methods), preferably the Powell method or the Simplex method with linear programming. After optimization, the parameters of the system can be fully determined (the modeled curve has been determined that best matches the empirical curve corresponding to the real data acquired), and the algorithm therefore provides access to a solution vector (R, Cs, Cp).

The conductivity of the sample is derived from this vector using the equation C=R/k defined above.

The second way to process the preprocessed time signal (see the right-hand part of FIG. 6) is for the FFT of the model of the liquid 42 to be inverted during a phase 45. The model of the liquid is then a time signal homogeneous with the preprocessed time signal. The two signals are compared in the same way as in the first method of determining the vector (R, Cs, Cp), based on a phase 43 of establishing a differential norm and an optimization phase 44.

The parameters are therefore known. The present invention nevertheless stores the vectors of three parameters associated with the measured temperature in a database during a learning phase 33 (see FIG. 4). The basic algorithm is therefore preferably provided with a library of prerecorded situations and can throughout its use enrich that database with results obtained from tests.

Storing a large number of situations enables acquisition of vectors (R, Cp, Cs) under normal conditions and under conditions where there is significant disturbance to one or more of the parameters R, Cp and Cs, for example the presence of an air bubble or a resin bead coming from the liquid purification system, followed by establishing polynomial functions linking R to Cp and Cs based on the parameters obtained in this way and used in the detection phase 35 described hereinafter.

Thus when the parameters of the sample have been determined, following the extraction phase 32, they are compared with the situations stored in the database during the detection phase 35. Using standard mathematical methods (standard deviation calculation, Gaussian error dispersion), the probability is then calculated of the vector (R, Cp, Cs) that has been determined belonging to a family of situations corresponding to a normal condition or to a disturbed condition, and, if so, which.

The behavior of the capacitances and the resistance is closely linked to the type of contamination. One example is the detection of an air bubble. The small size of the microelectrodes means that it is possible to detect the presence of air bubbles that falsify the resistance measurement and therefore the value of the conductivity of the solution. Thus in the presence of a bubble the resistivity of the liquid is affected by the resistivity of air. Note also that the values of the capacitances diverge. Note further that in this particular situation the value of the series capacitance tends to fall relative to a solution free of contamination whereas that of the parallel capacitance tends to rise. In the presence of a resin bead, the values of the capacitances vary very significantly and more than in the presence of an air bubble, whereas the value of the resistance remains substantially the same. The specific variations of these parameters are sufficiently large to be noteworthy and the risk of confusion with a sample free of contamination is eliminated by the comparison following the detection phase 35.

Once it has been determined that the parameters of the system belong to a given condition and their values have been determined, the alert and post-processing phase 36 provides access to the values of these parameters and/or to the value of the conductivity, for example on a display unit, and determines if the sample is contaminated or not and, if so, the type of contamination and how to remedy the problem. For example, the algorithm can trigger purging commands to restart the tests under better conditions.

A valuable application of this nonlimiting example of the present invention is to measuring the conductivity of a pure or ultrapure water solution, notably in water purification systems.

Numerous other variants are feasible as a function of circumstances, and the present invention is not limited to the example described and shown.

Note in particular that the microcontroller can be replaced by a generic processor or a dedicated digital signal processor (DSP). More generally, any electronic component comprising at least an arithmetic and logic unit will be suitable.

In applications other than the typical applications of detecting air bubbles or resin beads, the range of frequencies of the excitation signals can be different, in particular from 100 kHz to 20 MHz in applications that are more oriented toward life sciences (cytometry, identification of bacteria, etc.).

The invention claimed is:

1. A method for measuring the conductivity of a pure or ultrapure liquid using electrodes, comprising determining the conductivity by modeling the liquid in the form of an equivalent electrical circuit diagram comprising a resistor R, a capacitor Cp in parallel with the resistor R, and a series capacitor Cs,
applying series of reference excitation signals at different frequencies,
reconstructing the spectrum of the output signal by aggregating discrete measurements taken at the given frequencies,
comparing the reconstructed empirical signal with a theoretical model, and
minimizing the difference between the theoretical model and the empirical signal obtained to extract therefrom the triplet R, Cp, Cs.

2. The method according to claim 1, wherein the reconstructed spectrum of the output signal is subjected to temporal interpolation to increase the resolution of the signals at intermediate frequencies and/or to extrapolation of the frequencies in order to take into account frequencies that are inaccessible experimentally.

3. The method according to claim 1, wherein said comparison is effected between the Fourier transformed function of the reconstructed empirical temporal signal and the Fourier transform of the theoretical model or between the reconstructed empirical temporal signal and the inverse Fourier transform of a Fourier transform of the theoretical model.

4. The method according to claim 1, wherein said minimization step uses differential norm multidimensional non-linear minimization, preferably in the form of the Powell method or the Simplex method with linear programming.

5. The method according to claim 1, wherein it is further determined if the extracted triplet R, Cp, Cs corresponds to a situation of disturbance of the measurement and, if so, the nature of the disturbance.

6. The method according to claim 5, wherein said determination step uses a belonging probability calculation.

7. The method according to claim 5, wherein said disturbance corresponds to the presence of a foreign body, notably a particle, a non-miscible contaminant, or a gas bubble.

8. The method according to claim 1, wherein said excitation signals are applied in the form of pulses, preferably squarewave pulses.

9. The method according to claim 1, wherein the range of frequencies of the excitation signals is from 50 Hz to 5 kHz or from 100 kHz to 20 MHz.

10. The method according to claim 1, wherein said conductivity is measured by micro-electrodes.

11. The method according to claim 1, wherein said liquid is water.

12. A device for measuring conductivity of a pure or ultrapure liquid by means of electrodes, comprising a non-transitory computer-readable medium embodying instructions that when executed by a computing device cause the computing device to execute the method of claim 1.

13. The device according to claim 12, further comprising a microcontroller.

14. The device according to claim 13, wherein said microcontroller is connected to a conductivity measuring cell excited by a pulse generator or a reference signal generator.

15. The device according to claim 14, wherein said conductivity measuring cell is provided with micro-electrodes.

16. A water purification system comprising the device of claim 12, for measuring the conductivity of water.

* * * * *